United States Patent
Pell et al.

(10) Patent No.: US 10,809,160 B1
(45) Date of Patent: Oct. 20, 2020

(54) ENDOTRACHEAL TUBE SOUND

(71) Applicants: BN Intellectual Properties, Inc., Clearwater, FL (US); Mark Hoyt, Midvale, UT (US)

(72) Inventors: Donald M. Pell, St. Petersburg, FL (US); Mark Hoyt, Midvale, UT (US)

(73) Assignee: BN INTELLECTUAL PROPERTIES, INC., St. Petersburg, FL (US)

( * ) Notice: Subject to any disclaimer, the term of this patent is extended or adjusted under 35 U.S.C. 154(b) by 0 days.

(21) Appl. No.: 16/547,493

(22) Filed: Aug. 21, 2019

(51) Int. Cl.
*G01M 99/00* (2011.01)
*A61M 16/04* (2006.01)
*B08B 9/04* (2006.01)

(52) U.S. Cl.
CPC ........ *G01M 99/00* (2013.01); *A61M 16/0465* (2013.01); *G01M 99/005* (2013.01); *B08B 9/04* (2013.01)

(58) Field of Classification Search
CPC ........... B08B 9/04; B08B 9/027; A61B 90/70; A61B 2090/701; G01M 99/00; G01M 99/005
See application file for complete search history.

(56) References Cited

U.S. PATENT DOCUMENTS

| | | | | |
|---|---|---|---|---|
| 3,996,938 A * | 12/1976 | Clark, III | ............. | A61B 17/221 606/200 |
| 5,297,310 A * | 3/1994 | Cox | ......................... | A46B 5/06 15/104.2 |
| 5,709,691 A * | 1/1998 | Morejon | ............. | A61M 1/0078 128/207.14 |
| 5,768,741 A * | 6/1998 | Leiman | ..................... | B08B 9/00 15/104.05 |
| 5,897,567 A * | 4/1999 | Ressemann | ............ | A61B 17/32 604/22 |
| 5,964,004 A * | 10/1999 | Bean | ..................... | B08B 9/0436 15/104.05 |
| 5,987,683 A * | 11/1999 | Leiman | ..................... | B08B 9/00 15/104.16 |
| 6,045,623 A * | 4/2000 | Cannon | ................. | A61M 25/00 134/8 |
| 6,082,361 A * | 7/2000 | Morejon | ........... | A61M 16/0463 128/207.14 |
| 6,318,368 B1 * | 11/2001 | Morejon | ............. | A61M 1/0078 128/207.15 |
| 6,494,208 B1 * | 12/2002 | Morejon | ............. | A61M 1/0078 128/207.15 |
| 6,699,331 B1 * | 3/2004 | Kritzler | ................ | A61B 17/221 134/8 |

(Continued)

OTHER PUBLICATIONS

How to Make a Hematite (Magnetic) Bead Bracelet/Necklace. (Mar. 8, 2017). Retrieved from https://www.instructables.com/id/How-to-Make-a-Hematite-Magnetic-Bead-BraceletNe/ (Year: 2017).*

(Continued)

*Primary Examiner* — Alexander A Mercado
(74) *Attorney, Agent, or Firm* — Hauptman Ham, LLP

(57) ABSTRACT

An endotracheal tube sound device is presented having a sound bead connected to the distal end of a wire. A retaining piece is affixed to the wire adjacent to the sound bead. A handle is connected to the proximal end of the wire. Using this device, the sound bead may be inserted into an endotracheal tube to determine if the endotracheal tube is deformed and then removed from the endotracheal tube by pulling on the handle.

16 Claims, 13 Drawing Sheets

(56) References Cited

U.S. PATENT DOCUMENTS

| | | | | |
|---|---|---|---|---|
| 7,005,012 | B2* | 2/2006 | Bourrelly | B08B 9/049 134/22.12 |
| 8,566,995 | B2* | 10/2013 | Asano | A61B 1/122 15/104.16 |
| 9,687,391 | B2* | 6/2017 | Simon | A61F 13/36 |
| 9,968,247 | B2* | 5/2018 | Kaye | A61B 1/122 |
| 10,499,791 | B2* | 12/2019 | Seitz | A46B 5/00 |
| 10,537,695 | B1* | 1/2020 | Salinas | A61M 16/0463 |
| D880,093 | S* | 3/2020 | Hoftman | D32/40 |
| 2003/0209258 | A1* | 11/2003 | Morejon | A61M 1/0078 134/16 |
| 2003/0213501 | A1* | 11/2003 | Thomson | B08B 1/003 134/8 |
| 2005/0172971 | A1* | 8/2005 | Kolobow | A61M 16/0488 128/207.14 |
| 2006/0102200 | A1* | 5/2006 | Esquenet | B08B 9/04 134/22.1 |
| 2006/0130847 | A1* | 6/2006 | Morejon | A61M 16/0463 128/207.15 |
| 2007/0106302 | A1* | 5/2007 | Ortiz | A61B 1/01 606/108 |
| 2009/0044353 | A1* | 2/2009 | Galantai | B08B 9/0436 15/104.16 |
| 2010/0139018 | A1* | 6/2010 | Maslanka | A61B 1/122 15/104.05 |
| 2010/0163074 | A1* | 7/2010 | Hansen | A61B 90/70 134/8 |
| 2010/0186748 | A1* | 7/2010 | Morejon | A61M 16/0463 128/207.14 |
| 2010/0199448 | A1* | 8/2010 | Vazales | A61B 1/04 15/104.05 |
| 2011/0023885 | A1* | 2/2011 | Vazales | A61B 1/0669 128/207.14 |
| 2011/0289705 | A1* | 12/2011 | Asano | A61B 1/122 15/104.05 |
| 2013/0104884 | A1* | 5/2013 | Vazales | A61M 16/0418 128/202.16 |
| 2014/0150782 | A1* | 6/2014 | Vazales | A61M 16/0463 128/202.16 |
| 2015/0343182 | A1* | 12/2015 | Vazales | A61B 1/122 604/267 |
| 2020/0069472 | A1* | 3/2020 | Palushi | A61L 31/148 |

OTHER PUBLICATIONS

RounDuo. (May 1, 2016). Retrieved from https://www.potomacbeads.com/RounDuo-reg-Beads-s/3053.htm (Year: 2016).*

* cited by examiner

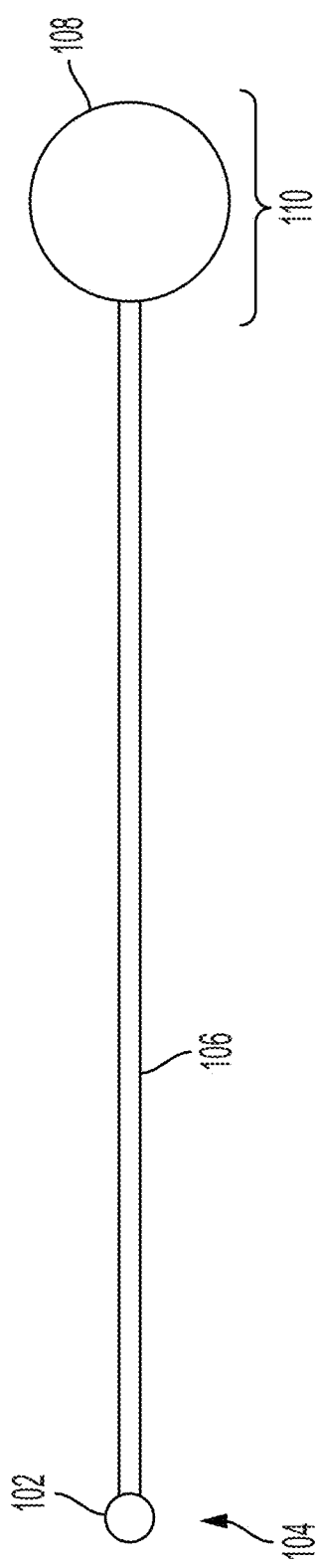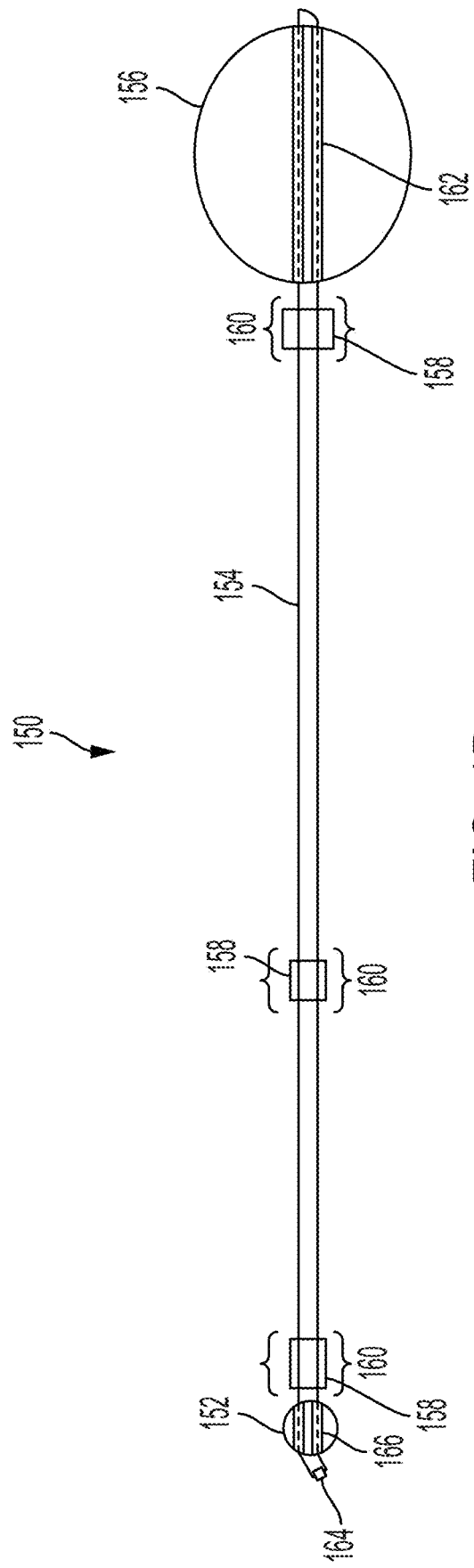

ENDOTRACHEAL TUBE SOUND

BACKGROUND

An endotracheal tube is a flexible plastic tube that is placed into a patient's airway, through the mouth into the trachea to help a patient breathe. The endotracheal tube is then connected to a ventilator, which delivers oxygen to the lungs. Because the plastic that forms the endotracheal tube, usually polyethylene or polyurethane, may soften when exposed to body heat and because the endotracheal tube follows a curved path from the mouth to the trachea, kinks and other deformations may form in the endotracheal tube, diminishing the airflow through the endotracheal tube. In order for deformations of the endotracheal tube to be detected, x-rays or other imaging may be performed.

BRIEF DESCRIPTION OF THE DRAWINGS

FIGS. 1A-B are views of an endotracheal tube sound device, in accordance with some embodiments.

DETAILED DESCRIPTION

Figure 2:
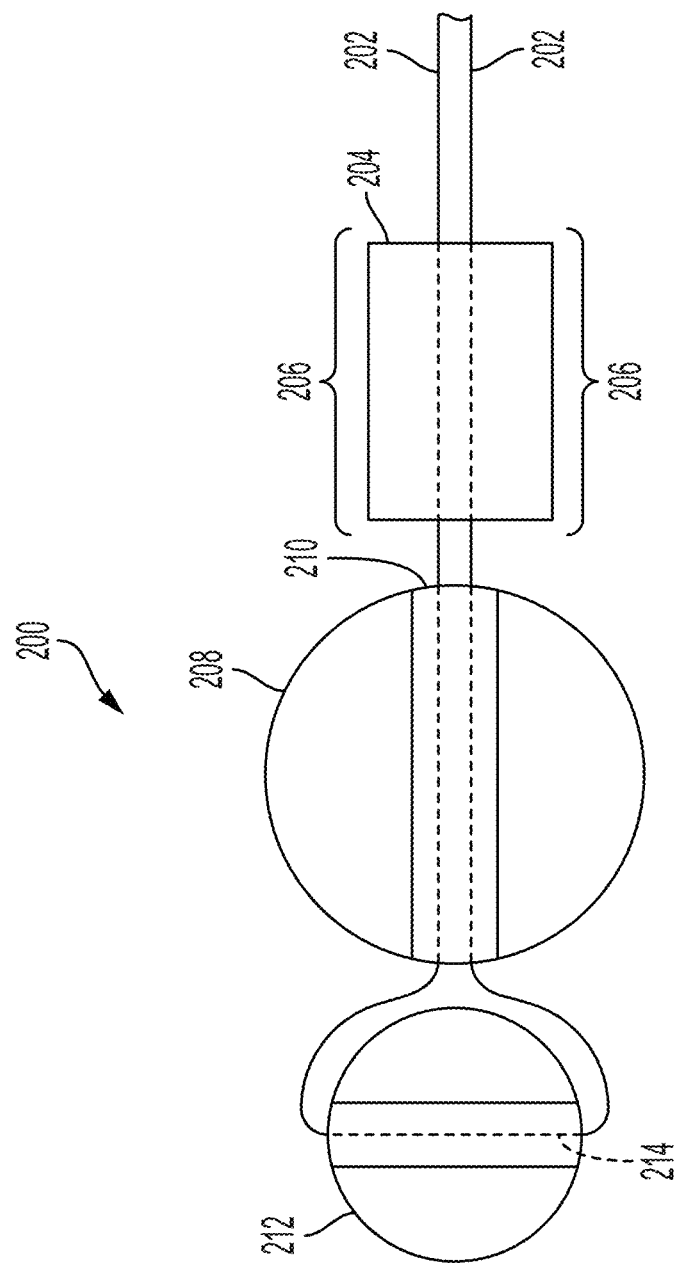
FIG. 2 is a view of an endotracheal tube sound bead and wire connection, in accordance with some embodiments.

The following disclosure provides many different embodiments, or examples, for implementing different features of the provided subject matter. Specific examples of components, values, operations, materials, arrangements, or the like, are described below to simplify the present disclosure. These are, of course, merely examples and are not intended to be limiting. Other components, values, operations, materials, arrangements, or the like, are contemplated. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 1A is a view of an endotracheal tube sound device 100, in accordance with some embodiments. Endotracheal tube sound device 100 has a sound bead 102 at a distal end 104 of a flexible device body 106 and a handle 108 at a proximal end 110 of the flexible device body 106. In some embodiments, endotracheal tube sound device 100 is made of a polymeric material such that the sound bead 102, the flexible device body 106, and the handle 108 are made of a same material by, e.g., a molding process. In some embodiments, endotracheal tube sound device 100 is made of multiple materials to provide resistance to breakage or loss of the sound bead 102 during a sound process of an endotracheal tube.

In some embodiments, the flexible device body includes at least one wire covered by a protective coating, and the handle and sound bead 102 include a polymeric material configured to retain an end of the wire extending through the flexible device body. In some embodiments, the flexible device body includes a single portion of polymeric material with no wire therein. In some embodiments, the sound bead 102 is configured with a single opening therein. In some embodiments, the sound bead 102 is configured with a plurality of openings therein. In some embodiments, the sound bead 102 is configured to pass a wire from the flexible device body through each of at least two openings in the sound bead 102, forming a loop of wire through the sound bead 102. In some embodiments, the sound bead 102 is retained on the wire by a retaining bead on an opposite side of the sound bead 102 from the flexible device body. In some embodiments, the flexible device body includes a single strand (or filament) of material. In some embodiments, the flexible device body includes multiple strands (or filaments) of material. In some embodiments, the flexible device body and the sound bead are a same material (e.g., a flexible device body material). In some embodiments, the flexible device body and the sound bead are different materials. In some embodiments, the flexible device body extends a length of the endotracheal tube sound device, and the sound bead is an enlarged portion of polymeric material of the flexible device body at a distal end of the endotracheal tube sound device. A sound bead has a proximal side oriented toward the majority of the flexible device body, and a distal side oriented away from the majority of the flexible device body. In some embodiments, the flexible device body extends through the sound bead. In some embodiments, a first portion of the flexible device body extends through the sound bead, and a second portion of the flexible device body extends through the sound bead, the first portion and the second portion of the flexible device body being discontinuous from each other along a length of the flexible device body. In some embodiments, a wire or filament of the flexible device body extends through an opening in the sound bead. In some embodiments, the sound bead has a distal side (oriented away, along the flexible device body) from the handle of the endotracheal tube sound device, where a filament, or a wire, of the flexible device body, protrudes in a loop from the sound bead.

In some embodiments, the handle includes a ball of material which encapsulates a portion of wire from the flexible device body. In some embodiments, sound bead 102 includes at least one opening to allow passage of a wire through the sound bead 102. In some embodiments, a wire from the flexible device body extends through a opening in a handle bead in two directions. In some embodiments, the wire from the flexible device body extends through a first opening in the handle bead, around a proximal side of the handle bead, and into a second opening back toward the flexible device body. In some embodiments, the handle is a loop of wire at a proximal end of the flexible device body.

With reference to FIG. 1B, an endotracheal tube sound device 150 is shown. A flexible device body 153 includes a wire, fiber or other flexible elongated material (e.g., a filament, a strand, a wire, or a coated wire) such as wire 154 inserted through a spherical or ellipsoidal sound bead 152 so that the distal end of the wire 154 is fixed by the sound bead 152. In some embodiments, the wire 154 is formed of stainless steel and coated with a polyamide material such as nylon. In some embodiments, the wire 154 is 0.025" in diameter. In some embodiments, the wire 154 is formed of a single strand or parallel strands of wire. In some embodiments, the sound bead 152 is formed of a polyacetal thermoplastic such as Delrin. In some embodiments, the sound bead 152 is between not less than 3 millimeters (mm) and not more than 8 mm in diameter. A sound bead 152 having a sound bead diameter of less than 4 mm has only one opening drilled through the bead. A sound bead 152 having a sound bead diameter of at least 4 mm but not more than 8 mm has two openings drilled through the sound bead 152. The wire 154 may pass through a sound bead opening 166 and through a clip or small retaining bead 164, to secure the sound bead 152 to the wire 154. The wire 154 may pass through a sound bead opening 166 and around a portion of a distal side of the sound bead to hold the sound bead on the flexible device body. In some embodiments, a sound bead with a single opening therein is configured to receive, through the sound bead opening, two strands (e.g., of wire) or filaments of a flexible device body. In some embodiments, a sound bead with two openings therein is configured to receive, through each opening, a single strand (e.g., of wire) or filament of a flexible device body. A distal retaining piece 158 (or, a sound bead retaining piece) may crimp or otherwise hold the wire 154, abutted to the sound bead 152 at the proximal side of sound bead 152 so that the sound bead 152 cannot move along the wire. In some embodiments, the distal retaining piece 158 is formed of stainless steel. In some embodiments, the distal retaining piece is formed of a polymeric material. In some embodiments, the distal retaining piece is formed of a cured material added to a loop of wire protruding from the opening in the sound bead, such that the loop is encapsulated by the cured material. In some embodiments, the distal retaining piece 158 is 0.25" in length, although other lengths are contemplated to be within the scope of the present disclosure. In some embodiments, the length of the distal retaining piece ranges from 1 mm to 6 mm, although other lengths are also contemplated to be within the scope of the present disclosure. The length of the distal retaining piece is such that, upon reaching a curve in an endotracheal tube, the sound bead is able to pass around a curve in an endotracheal tube without being bound or retained by the distal retaining piece as the sound bead reaches the curve. In some embodiments, a protective coating 160 surrounds the distal retaining piece 158 to present a smooth exterior surface with no sharp corners or edges to scratch the patient or the wall of the endotracheal tube. In some embodiments, the protective coating 160 includes a heat-shrinking material which covers the body and ends of the distal retaining piece. In some embodiments, the protective coating is a coating of material which is sprayed or applied to the distal retaining piece in liquid form before curing to solidify on the distal retaining piece. In some embodiments, further distal retaining pieces 158 with protective coatings 160 are placed along the length of the wire, to prevent the strands of wire from separating. A handle bead 156, larger in diameter than the sound bead 152 may be attached to the proximal end of the wire 154 through openings 162 in the handle bead 156. In some embodiments, the handle bead is larger than the interior diameter of the endotracheal tube in which the endotracheal tube sound device is inserted to prevent the sound from fully entering the tube. In some embodiments, the length of the endotracheal tube sound device is less than the length of the endotracheal tube to prevent the distal end of the endotracheal tube sound device from exiting a distal end of the endotracheal tube. A chance of the sound bead detaching from the endotracheal tube sound device increases when the sound bead exits the distal end of the endotracheal tube. The handle bead 156 allows the practitioner to comfortably hold onto the endotracheal tube sound device 150 so it may be easily removed from the patient's airway.

When an endotracheal tube is inserted into a patient's trachea, it becomes difficult to see whether the endotracheal tube has kinked or otherwise deformed. A kink or other deformation of the endotracheal tube causes the inner diameter of the endotracheal tube to decrease, and the smaller inner diameter at the location of the kink or deformation makes breathing more difficult for the patient. By inserting the sound bead 152 at the distal end of the wire 154 into the endotracheal tube and applying minimal force to cause the sound bead 152 to descend along the endotracheal tube, resistance will be felt as the sound bead 152 encounters a deformation that has reduced the diameter of the endotracheal tube to a diameter smaller than the diameter of the sound bead 152. This allows the practitioner to detect a blocked endotracheal tube without using an x-ray to radiologically observe the profile of the endotracheal tube in the throat. The distorted endotracheal tube can then be removed and replaced so that the patient can receive the necessary breathing assistance from a ventilator.

With reference to FIG. 2, an endotracheal tube sound bead and wire connection 200 is shown, in accordance with an embodiment. A wire 202 passes through a opening 210 in a sound bead 208. In some embodiments, the sound bead 208 is 3 mm in diameter. According to some embodiments, a sound bead 208 diameter smaller than 3 mm is not used in an endotracheal tube sounding device because a sound bead 208 diameter smaller than 3 mm is too small to have openings formed therein to receive the wire from a flexible device body. On the distal end of the sound bead 208, the wire 202 passes through a perpendicular opening 214 in a retaining bead 212 and then back through opening 210 in the sound bead 208. In some embodiments, the retaining bead is 2 mm in diameter. A retaining piece 204 with a protective coating 206 firmly clamps the wire 202 near the sound bead 208 so that the sound bead 208 does not move along the wire 202.

Figure 3:
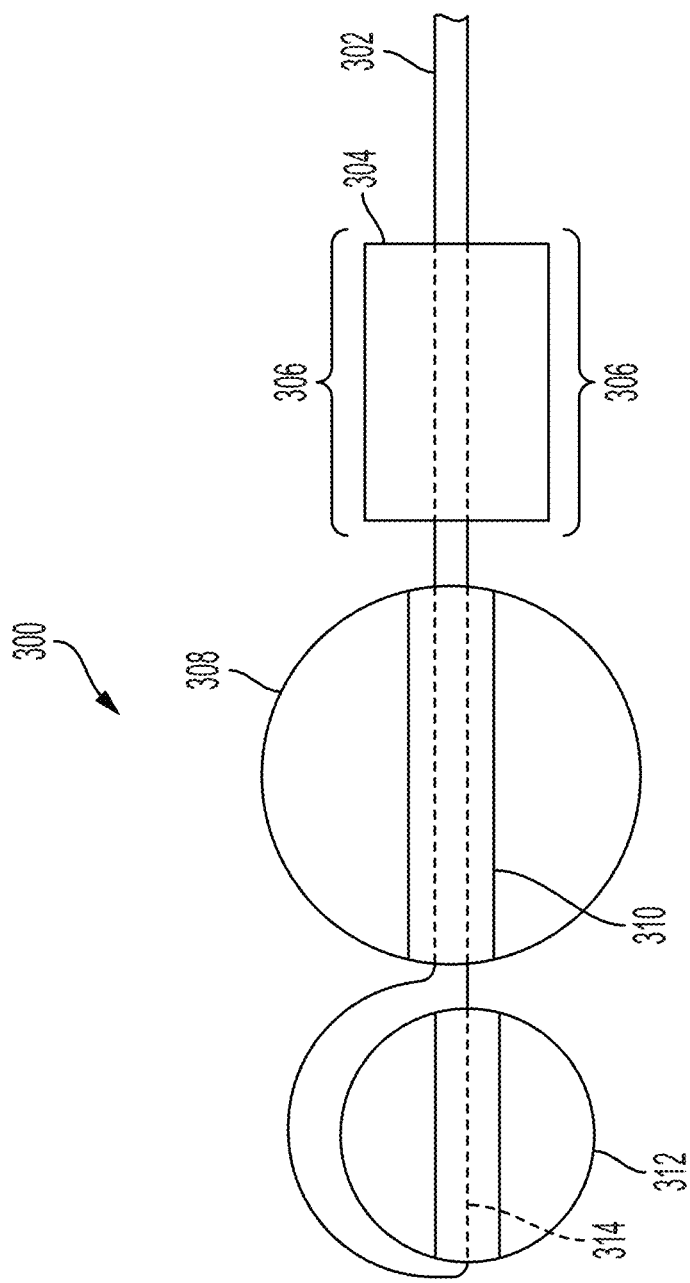
FIG. 3 is a view of an endotracheal tube sound bead and wire connection, in accordance with some embodiments.

With reference to FIG. 3, an endotracheal tube sound bead and wire connection 300 is shown, in accordance with an embodiment. A wire 302 passes through a opening 310 in a sound bead 308. On the distal end of the sound bead 308, the wire 302 passes through a parallel opening 314 in a retaining bead 312 and then back through opening 310 in the sound bead 308. A retaining piece 304 with a protective coating 306 firmly clamps the wire 302 near the sound bead 308 so that the sound bead 308 is unable to move along the wire 302.

Figure 4:
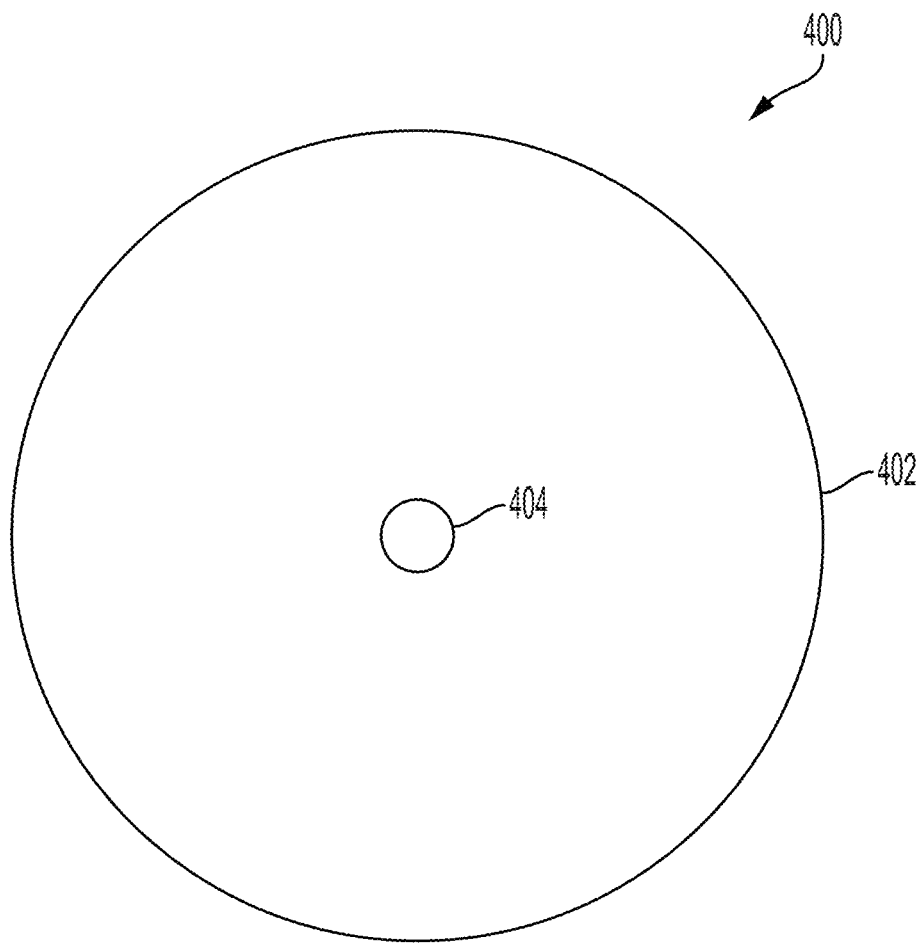
FIG. 4 is a top view of an endotracheal tube 3 mm sound bead, in accordance with some embodiments.

With reference to FIG. 4, an endotracheal tube 3 mm sound bead 400 is shown, in accordance with an embodiment. Because a 3 mm bead 402 is so small, a single opening 404 is drilled through the 3 mm bead 402.

Figure 5:
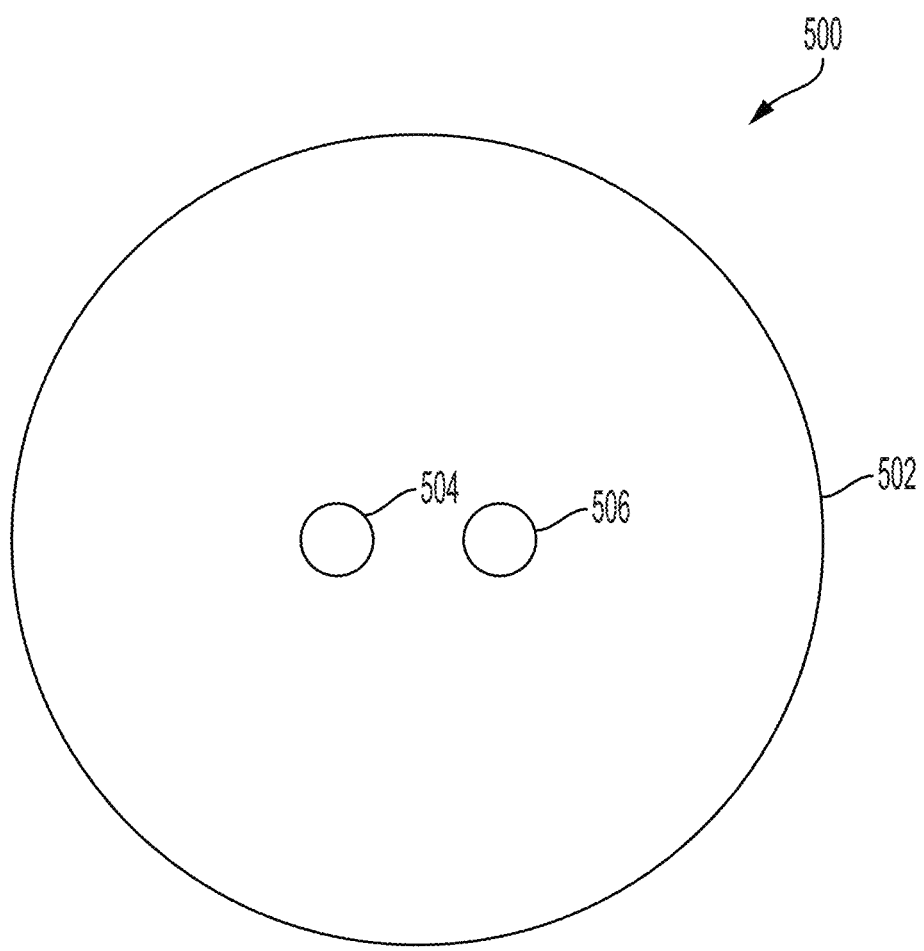
FIG. 5 is a top view of an endotracheal tube 4-8 mm sound bead, in accordance with some embodiments.

With reference to FIG. 5, an endotracheal tube 4-8 mm sound bead 500 is shown, in accordance with an embodiment. Because the 4-8 mm bead 502 is larger, two openings 504 and 506, are drilled through the 4-8 mm bead 502.

Figure 6:
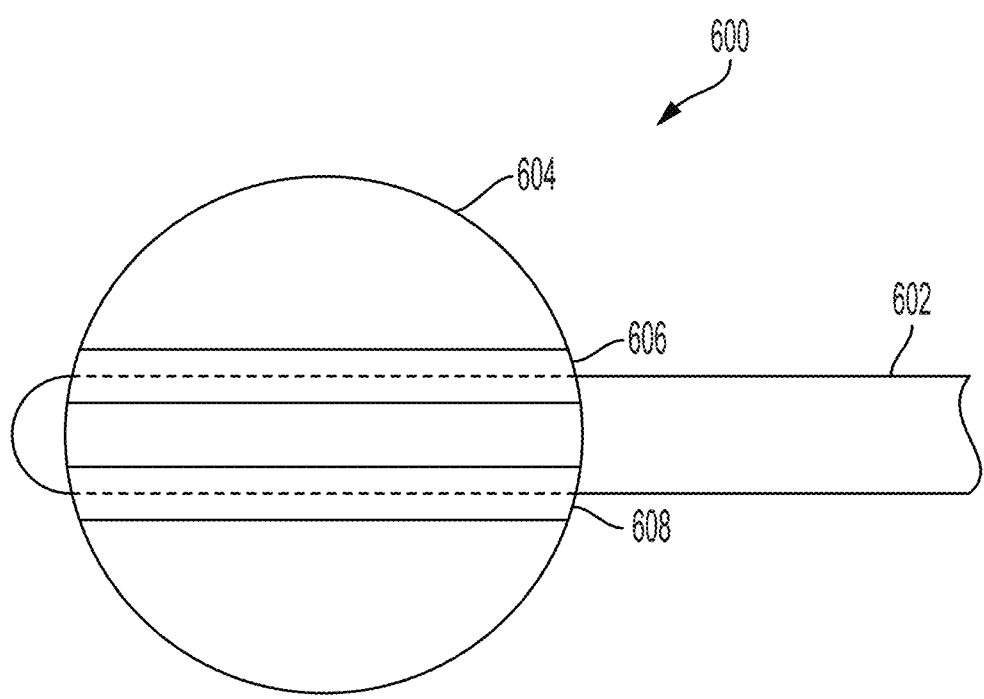
FIG. 6 is a top view of an endotracheal tube sound bead wire configuration, in accordance with some embodiments.

With reference to FIG. 6, an endotracheal tube sound bead wire configuration 600 is shown, in accordance with an embodiment. A 4-8 mm bead 604 with a first opening 606 and a second opening 608 has a wire 602 passed through the first opening 606 and back through the second opening 608.

Figure 7:
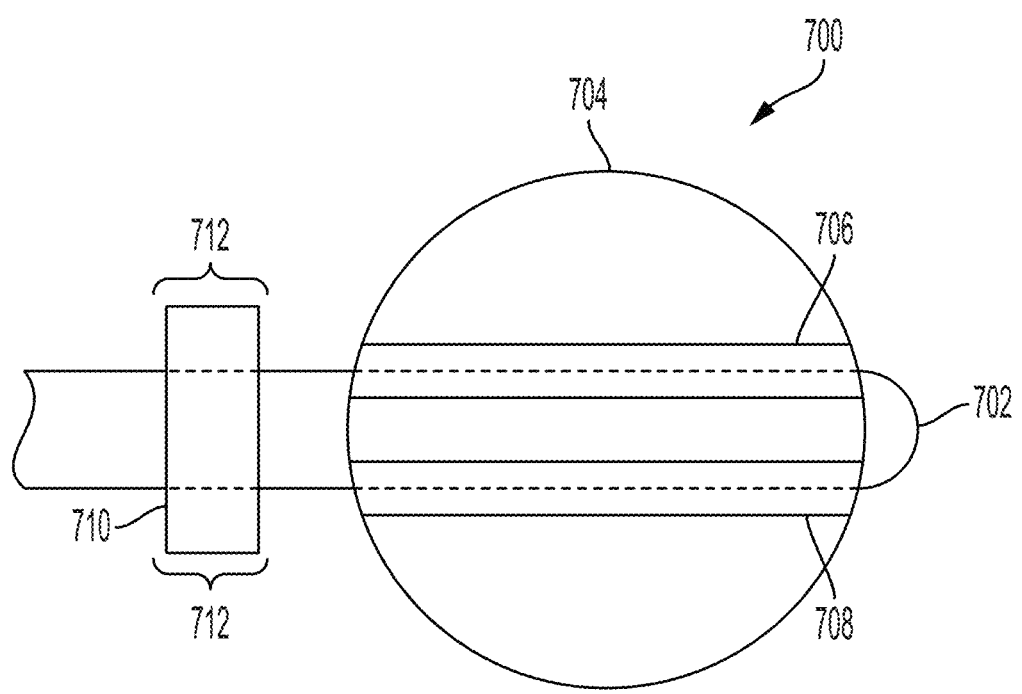
FIG. 7 is a top view of an endotracheal tube sound bead wire configuration, in accordance with some embodiments.

With reference to FIG. 7, an endotracheal tube sound bead wire configuration 700 is shown, in accordance with an embodiment. A 4-8 mm bead 704 with a first opening 706 and a second opening 708 has a wire 702 passed through the first opening 706 and back through the second opening 708. A retaining piece 710 crimps or otherwise holds the wire so that the 4-8 mm bead 704 cannot move along the wire 702. In some embodiments, retaining piece 710 has a protective coating 712.

Figure 10:
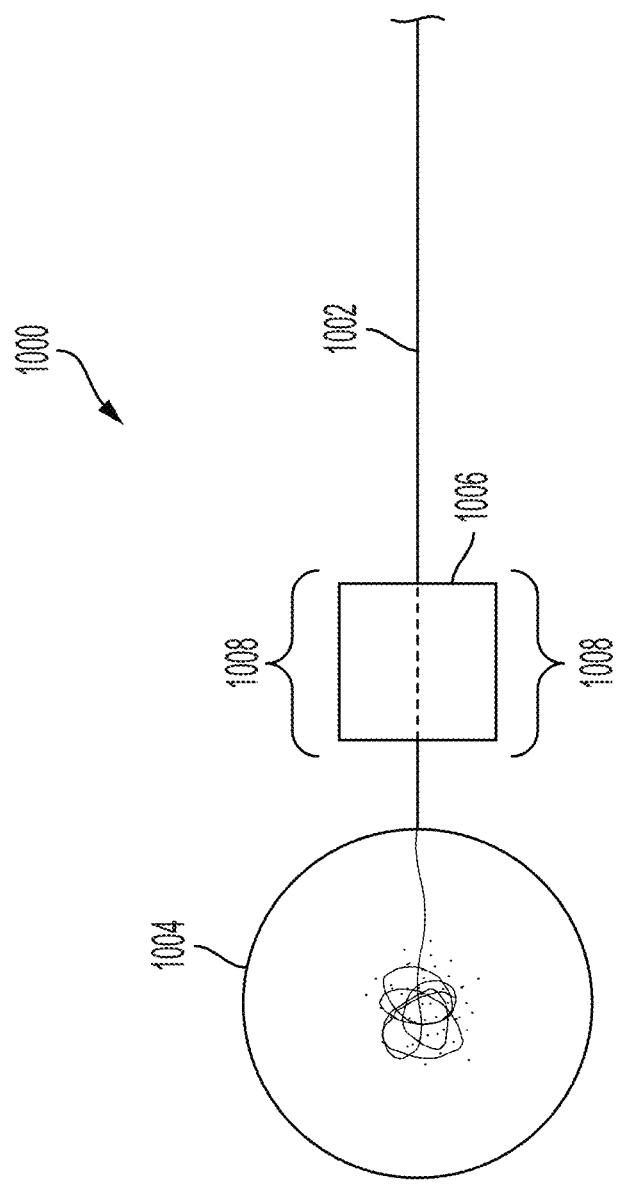
FIG. 10 is a top view of an endotracheal tube sound bead wire configuration, in accordance with some embodiments.

With reference to FIG. 10, an endotracheal tube sound bead wire configuration 1000 is shown, in accordance with an embodiment. A knotted wire 1002 has a sound bead 1004 formed over a knot or end piece. A retaining piece 1006 crimps or otherwise holds the wire 1002 so that the wire 1002 is not easily removed from the sound bead 1004. In some embodiments, the retaining piece 1006 has a protective coating 1008.

Figure 13:
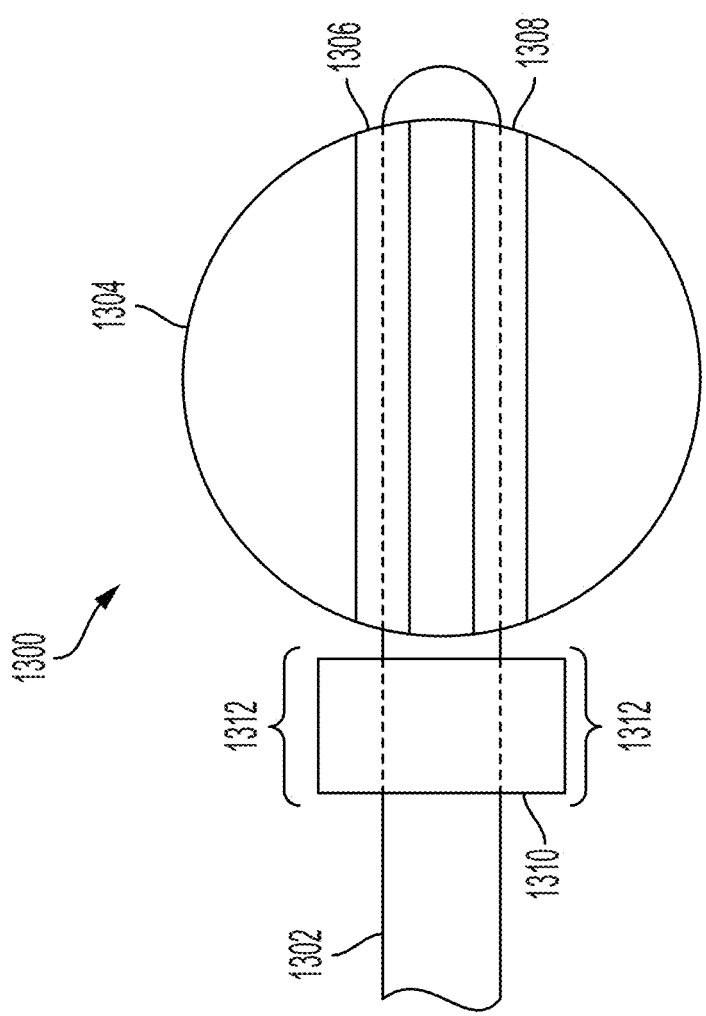
FIG. 13 is a top view of an endotracheal tube sound handle, in accordance with some embodiments.

With reference to FIG. 13, an endotracheal tube sound handle 1300 is shown, in accordance with an embodiment. A handle bead 1304 with a first opening 1306 and a second opening 1308 has a wire 1302 passed through the first opening 1306 and back through the second opening 1308. In some embodiments, the handle bead is about 19 mm in diameter. A retaining piece 1310 crimps or otherwise holds the wire 1302 so that the handle bead 1304 cannot move along the wire 1302. In some embodiments, retaining piece 1310 has a protective coating 1312.

Figure 8:
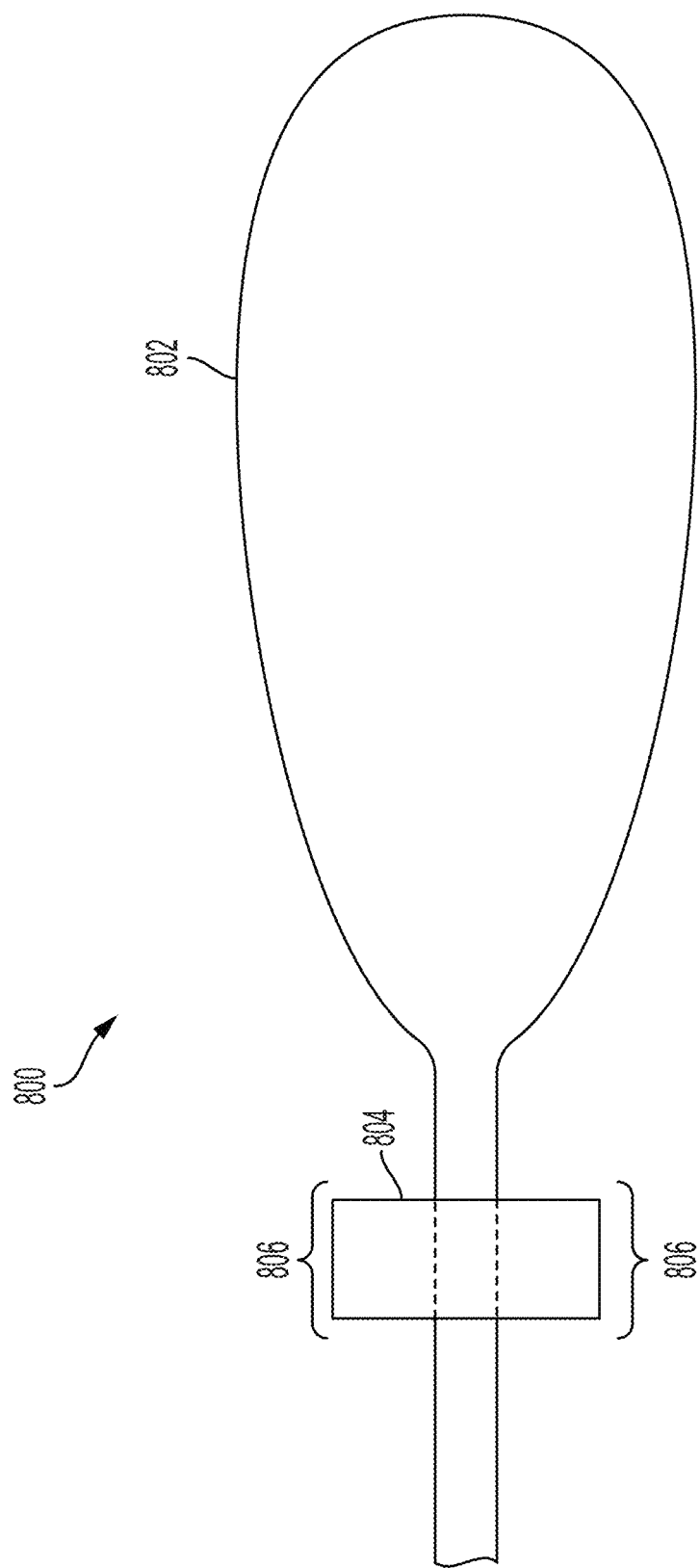
FIG. 8 is a top view of an endotracheal tube sound handle, in accordance with some embodiments.

With reference to FIG. 8, an endotracheal tube sound handle 800 is shown, in accordance with an embodiment. A wire 802 forms a loop that is large enough for the practitioner's hand to fit through. The wire 802 passes through a loop retaining piece 804 that crimps or otherwise holds the wire so that the loop does not change size. In some embodiments, the loop retaining piece 804 has a protective coating 806.

Figure 9:
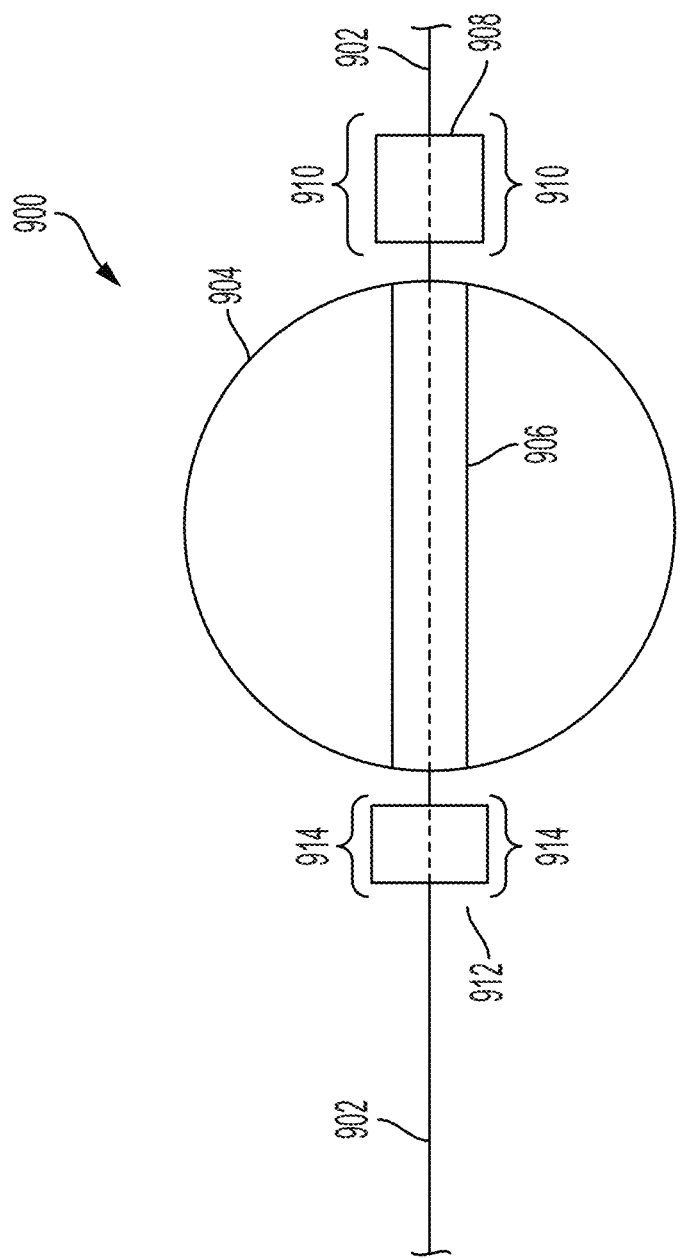
FIG. 9 is a top view of an endotracheal tube sound handle, in accordance with some embodiments.

With reference to FIG. 9, an endotracheal tube sound handle 900 is shown, in accordance with an embodiment. A handle bead 904 with a opening 906 has a wire 902 passed through the opening 906. The wire 902 at the proximal end of the handle bead 904 is secured by a proximal retaining piece 908 that crimps or otherwise holds the wire 902. In some embodiments, the proximal retaining piece 908 has a protective coating 910. The wire 902 at the distal end of the handle bead 904 is secured by a distal retaining piece 912 that crimps or otherwise holds the wire 902 in place so that the handle bead 904 is unable to move along the wire 902. In some embodiments, the distal retaining piece 912 has a protective coating 914.

Figure 11:
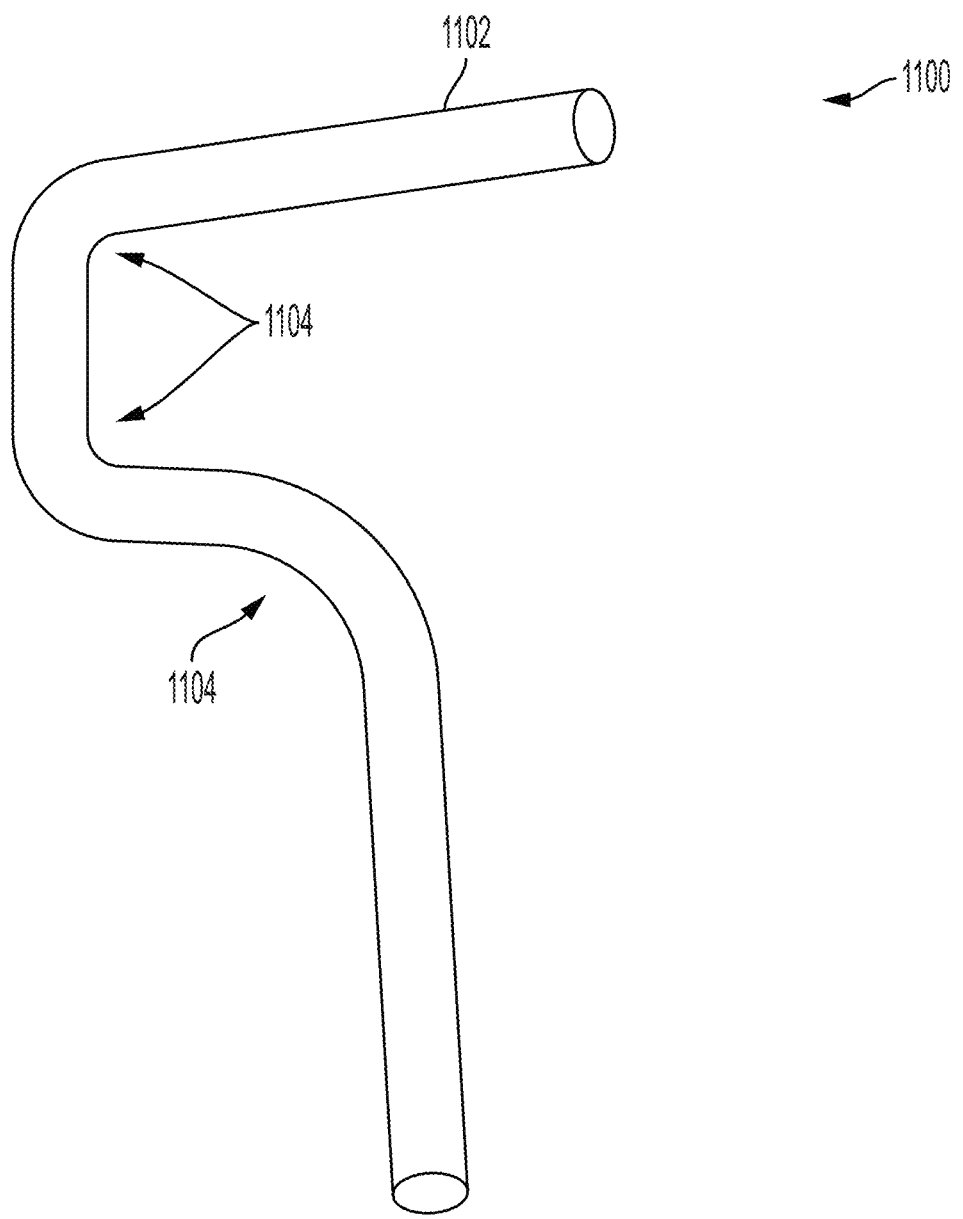
FIG. 11 is a top view of an endotracheal tube arrangement, in accordance with some embodiments.

With reference to FIG. 11, an endotracheal tube arrangement 1100 is shown, in accordance with an embodiment. The plastic endotracheal tube 1102, after being inserted into a patient's airway, follows the curve over the tongue and back to the trachea. Curves 1104 of the endotracheal tube 1102 correspond to curves in the patient's airway. At some points along the plastic endotracheal tube 1102, as the plastic warms to body temperature, the plastic endotracheal tube 1102 may become kinked or otherwise distorted. Kinks in the endotracheal tube tend to occur at locations of curves 1104 in the endotracheal tube.

Figure 12:
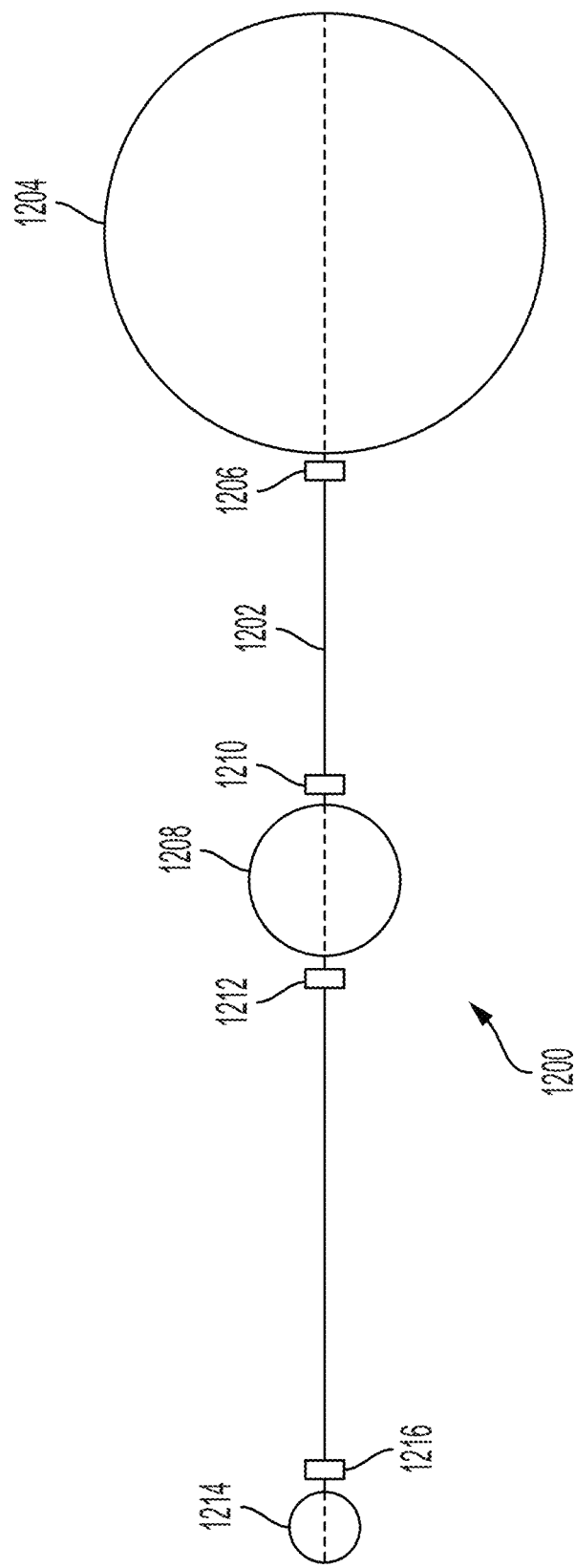
FIG. 12 is a top view of an endotracheal tube sound device, in accordance with some embodiments.

With reference to FIG. 12, an endotracheal tube sound device 1200 is shown. A sound bead 1214 is connected to a wire 1202. The sound bead may be held in place with a distal retaining piece 1216. A limiting bead 1208, typically larger than the diameter of an endotracheal tube, is placed at a distance (a limiting bead distance) from the sound bead 1214 such that the sound bead is prevented from moving past the distal end of the endotracheal tube and into the patient's lung. The limiting bead 1208 is held in place by two limiting bead retaining pieces 1210 and 1212. A handle bead 1204 is affixed to the proximal end of the wire 1202 and is held in place by a proximal bead retaining piece 1206. The limiting bead 1208 is held at a limiting bead retaining distance from the sound bead 1214, where the limiting bead retaining distance is not greater than the length of the endotracheal tube.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An endotracheal tube sound device comprising:
    a flexible device body;
    a sound bead on the flexible device body;
    a handle at an end of the flexible device body and configured to remove the sound bead from an endotracheal tube, and
    a retaining bead at a distal side of the sound bead from the handle, wherein
        the sound bead has a diameter of at least 3 millimeters (mm) and not more than 8 mm,
        the sound bead has a first opening passing through the sound bead, the opening having a diameter of at least two times a diameter of the flexible device body, and
        the flexible device body passes through the sound bead two times, through a retaining bead opening in the retaining bead one time, and around the retaining bead one time.

2. The endotracheal tube sound device of claim 1, wherein the flexible device body further comprises a wire and further comprising a sound bead retaining piece affixed to the flexible device body adjacent to the sound bead.

3. The endotracheal tube sound device of claim 1, wherein the retaining bead opening is perpendicular to the sound bead opening.

4. The endotracheal tube sound device of claim 1, wherein the retaining bead opening is parallel to the sound bead opening.

5. The endotracheal tube sound device of claim 1, wherein
- the sound bead further comprises a second opening extending through the sound bead, and
- the flexible device body further comprises a wire, the wire passing through the first sound bead opening, through the second sound bead opening, and through a sound bead retaining piece.

6. The endotracheal tube sound device of claim 1, wherein the handle is a handle bead connected to the end of the flexible device body distal from the retaining bead.

7. The endotracheal tube sound device of claim 6, wherein two handle bead openings extend through the handle bead.

8. The endotracheal tube sound device of claim 6, wherein one handle bead opening extends through the handle bead.

9. The endotracheal tube sound device of claim 1, wherein the handle further comprises a loop of flexible device body material.

10. The endotracheal tube sound device of claim 9, further comprising a loop retaining piece holding the end of the flexible device body distal from the sound bead in the loop to form the handle.

11. The endotracheal tube sound device of claim 2, further comprising a protective coating over each sound bead retaining piece.

12. The endotracheal tube sound device of claim 1, wherein the sound bead is spherical.

13. The endotracheal tube sound device of claim 1, further comprising a limiting bead on the flexible device body at a limiting bead distance from the sound bead, the limiting bead being configured to prevent the sound bead from passing beyond an end of an endotracheal tube after insertion into the endotracheal tube.

14. The endotracheal tube sound device of claim 13, further comprising at least one limiting bead retaining piece configured to hold the limiting bead at a limiting bead retaining distance from the sound bead.

15. The endotracheal tube sound device of claim 1, wherein the handle further comprises a handle bead having two handle bead openings therethrough, wherein the flexible device body extends from the sound bead, through a first handle bead opening, around an end of the handle bead distal to the flexible device body, and through a second handle bead opening toward the sound bead.

16. The endotracheal tube sound device of claim 1, wherein the handle further comprises a handle bead having one handle bead opening, wherein the flexible device body extends from the sound bead through the handle bead opening, and the flexible device body is retained within the handle bead opening by a handle bead retaining piece on the flexible device body on each side of the handle bead opening.

* * * * *